United States Patent [19]

Lustig

[11] Patent Number: 4,472,140
[45] Date of Patent: Sep. 18, 1984

[54] BITE REGISTRATION DEVICE

[76] Inventor: Leopold P. Lustig, 304 Greenwood St., Newton Centre, Mass. 02159

[21] Appl. No.: 72,001

[22] Filed: Sep. 4, 1979

Related U.S. Application Data

[63] Continuation-in-part of Ser. No. 840,492, Oct. 7, 1977.

[51] Int. Cl.³ .............................................. A61C 9/00
[52] U.S. Cl. ......................................... 433/38; 433/71
[58] Field of Search ..................... 433/38, 37, 71, 214, 433/46

[56] References Cited

U.S. PATENT DOCUMENTS

| | | | |
|---|---|---|---|
| 1,979,493 | 11/1934 | Salvio | 433/38 |
| 2,713,202 | 7/1955 | Jones | 433/38 |
| 3,468,029 | 9/1969 | Moore | 433/38 |
| 3,501,837 | 3/1970 | Clark | 433/38 |
| 3,534,475 | 10/1970 | Hilaire | 433/37 |
| 3,537,179 | 11/1970 | Parker et al. | 433/214 |
| 3,574,259 | 4/1971 | Jones | 433/38 |
| 3,604,116 | 9/1971 | Shpuntoff | 433/71 |
| 3,882,601 | 5/1975 | Jahn | 433/214 |
| 3,903,602 | 9/1975 | Jones | 433/38 |
| 4,161,067 | 7/1979 | Bekey et al. | 433/42 |

Primary Examiner—John J. Wilson
Attorney, Agent, or Firm—Alfred H. Rosen

[57] ABSTRACT

A carrier for introducing bite registration material between occlusal surfaces of teeth, comprising a frangible film weakened to minimize its ability to stimulate the proprioceptive neuromuscular mechanism associated with jaw motions.

8 Claims, 8 Drawing Figures

BITE REGISTRATION DEVICE

BACKGROUND OF THE INVENTION

This invention relates to bite registration in the human mouth, and particularly to the task of obtaining a bite registration with the jaws in true centricity upon occlusion of the teeth, as is required for example in producing good fitting dentures. The problem is well recognized and prior attempts to solve it are described in patents of Jones, U.S. Pat. Nos. 2,713,202; 3,574,259; and 3,987,548, among others. Jones uses bibs of gauze to carry impression paste. Beck U.S. Pat. No. 4,003,132 is another example of the use of textile web to carry dental impression medium, on one or both sides of the web. An earlier patent of Lucia, U.S. Pat. No. 2,633,637 describes a high-spot marker using a textile, paper or cellophane coated on one or both sides with a soft wax to cover a marking material. Shpuntoff U.S. Pat. No. 3,604,116 describes a proposed improvement in the high spot marker of Lucia wherein the carrier for bite waxes and the like is made of a strong pliable sheet of material having a thickness of less than 0.020 mm. The mechanical strength of the sheet material must be much greater than that of the impression material (column 1, lines 50–56); metallic foils of gold and aluminum, and non-metallic plastic foils are suggested. It is asserted that thicker carriers for the impression material disturb the normal bite, and reliance is placed on the elastic compressibility of the periodontal membranes which separate the roots of the teeth from the bones of the jaws. Specifically, Shpuntoff states (column 1, lines 38–44) that the membranes have normal thickness of about 0.030 to 0.035 mm. and can be reduced in thickness by slightly less than 0.010 mm. by forces available in biting so that a separation of the upper and lower teeth by less than 0.020 mm. may be compensated by compression of the periodontal membranes.

GENERAL NATURE OF THE INVENTION

I have discovered that the prior art bite registration devices are deficient in that they ignore the proprioceptive neuromuscular mechanism controlling jaw motions. Reference is made, for example, to "Current Clinical Dental Terminology" Boucher-Editor, published by The C.V. Mosley Company, Saint Louis, 1974, pages 316 and 317, where the terms "proprioceptors" and "proprioceptive neuromuscular mechanism" are defined as follows:

"proprioceptors—Sensory nerve receptors situated in the muscles, tendons, and joints that furnish information to the central nervous system concerning the movements and positions of the limbs, the trunk, the head and neck, and more specifically for the dentist, the mandible and its associated oral structures. As a result of these stimuli received by the nerve centers, the contractions of individual muscles and groups of muscles are coordinated to produce smooth, finely adjusted, effective movements that would be impossible in the absence of such information."

"proprioceptive neuromuscular mechanism—A biomechanical hookup of sensory and motor nerve trunk lines that control or help automate the muscular activities of posture. The muscular sensation and memory of jaw motions, relations, and positions in space should be studied to understand better the disorderly actions (ataxia) of the mandible. Appreciation of the automaticity of gnathic procedure grows as the student studies the well-ordered relations of the organically fit mouth (eutaxia). The outer informants of jaw movements and positions are receptors in the periodontium, the jaw joint capsules, and the important chewing muscles. What these reporters discover is "wired" to centers in either the brain or the spinal cord. These centers of recorded neural learning command the effectors to care for the needs of the jaw, if possible, by stimulating the correct controls of jaw action. Even after the effectors begin, other signals from receptors such as those of touch, pain, and pressure join with the proprioceptors in monitoring both further corrections of the amount of force and the directions in which the vector is running. Such monitoring is called feedback. (Gnathol.)"

Without taking the proprioceptor nerves into account, fine adjustments in bite registration cannot be made. Even a single human hair between two occluding teeth will alter the true bite. A film that is as much as 0.020 mm. thick, which compresses the periodontal membranes as much as 0.010 mm., will stimulate the sensory nerve receptors situation in the vicinity and thereby will alter the contractions of individual muscles and groups of muscles so that the true bite will be altered, however minutely. For that reason, a carrier for impression material which is made of a gauze or other fiber material whether woven or non-woven, or of a film, which exerts a back pressure on the periodontal membranes, is not suitable for taking impressions with the highest fidelity to the existing bite of a patient.

Contrary to the teachings of the prior art, the present invention proposes a carrier for impression material which imposes the least possible stimuli on the proprioceptors. One example is a frangible film of a plastic material perforated over the major portion of its area so that it is largely foraminous. Such a carrier can be coated on one or both sides with impression material and, when placed in the mouth, will function primarily as a carrier for the impression material, and will exert a minimum of reactive force on the impression material in response to interdental pressure.

DETAILED DESCRIPTION OF THE DRAWINGS

Figure 1:
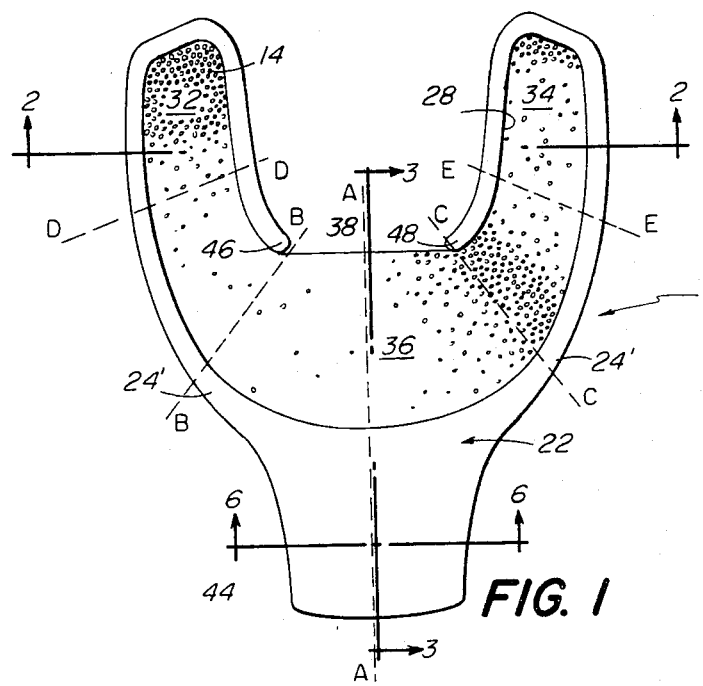
FIG. 1 is a plan view of a full dental-arch bite registration device according to the invention.
Figure 3:
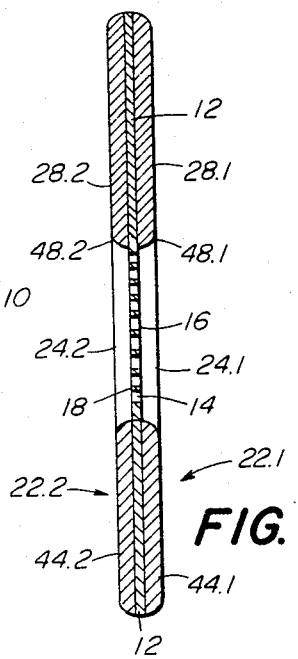
FIG. 3 is a section on line 3—3 of FIG. 1.
Figure 2:
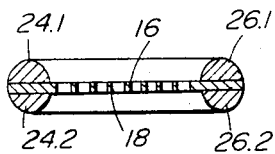
FIG. 2 is an enlarged section on line 2—2 of FIG. 1.
Figure 2:
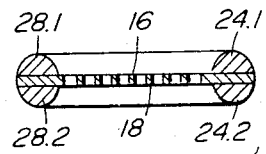
Figure 4:
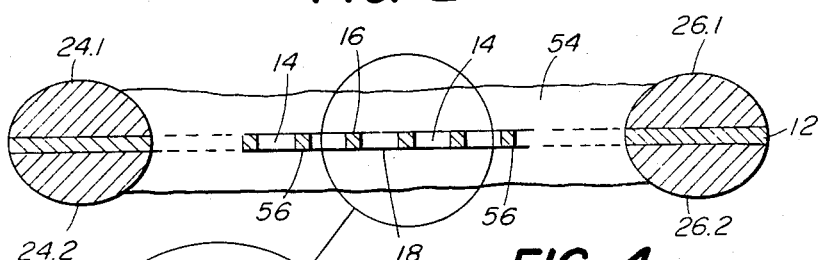
FIG. 4 is a further enlarged portion of FIG. 2 showing a bite-registration material on the device.
Figure 5:
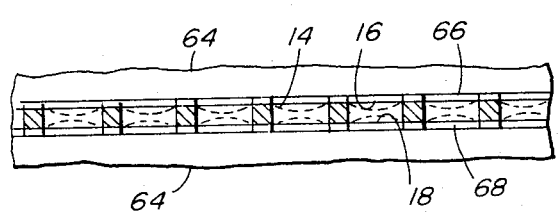
FIG. 5 is a view like FIG. 4 showing a bite registration wax on the device.
Figure 5:
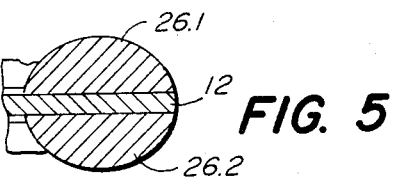

FIGS. 1 to 3, inclusive, show a carrier 10 for bite registration material (shown in FIGS. 4 and 5). A foraminous film 12 has perforations 14 over the major portion of its surfaces 16, 18. A frame 22 is affixed to the film at its entire outer periphery 24 and at the quadrant portions 26, 28 of its inner periphery. The frame at the outer periphery 24 is shaped to the outer periphery of a full dental arch; at the inner periphery portions 26, 28 the frame is shaped to the inner periphery of the respective posterior quadrants. The film 12 is generally U-shaped and spans the frame across the regions 32, 34 of the lateral posterior teeth, that is, at the quadrants, and extends from the frame at the outer periphery 24 in the region 36 of the anterior teeth toward the frame at the inner periphery 26, 28, where the film has a free edge 38 extending between two free ends 46, 48 of the frame. A handle 44 extends from the frame at its outer anterior periphery 24, in the region 36 of the anterior teeth.

As is apparent in FIGS. 2 and 3, the frame 22 can be made in two like parts 22.1 and 22.2 between which the film 12 is held, as in a sandwich. The frame parts 22.1 and 22.2 can be made of any of several suitable materials, such as plastics, paper or metal foils. The frame parts 22.1 and 22.2 can be attached to the film by any suitable adhesive material that is non-toxic. In the case or cases where the film and frame parts are made of the same material, they can be integral. If both are of the same thermoplastic material, they can be attached by heating the frame parts and film between them to the temperature at which they will fuse or can be pressed together, and then cooling them; i.e.: by a form of plastic welding. FIG. 3 shows the device as it appears in side view in the region 34 of one quadrant, where the frame parts 28.1 and 28.2 at the inner periphery support the film 12, these parts terminating in the free ends 48.1 and 48.2. The handle 44 is also in two parts 44.1 and 44.2 with the film 12 between them; although the film 12 is shown without perforations in the handle portion, it can be perforated in which case any adhesive cement or the like used to attach the frame parts to the film would pass through the perforations and fasten tne frame parts directly together.

Figure 6:
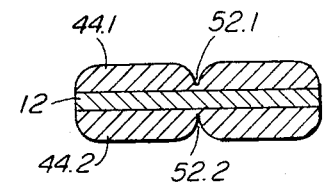
FIG. 6 is a section along line 6—6 of FIG. 1.

The device can be made for full dental-arch bite registration, with provision for separating it into sections that can be used for partial-arch bite registration, as is shown in FIG. 1. Dashed lines A—A, B—B, C—C, D—D, and E—E each traversing the device 10 from the outer periphery 24 to the inner periphery, represent lines along which the device can be weakened, or cut, for separating it into such sections. Thus, if parted on line A—A, the device will provide two half-sections each with a portion of the handle 44, suitable for right-half-arch, or left-half-arch bite registration. Likewise, if parted on line B—B or C—C the device will provide a smaller portion suitable for taking a bite-registration impression of a quadrant, including bicuspids or pre-molars, and molars. In this case, the frame at the outer periphery will extend forward so that the frame end 24' formed at the parting line can be used as a handle. Further, a smaller section parted on line D—D or E—E would oe useful for taking an impression of a partial quadrant consisting of molars. The frame 22 can be weakened along lines A—A, B—B, C—C, D—D and E—E, to facilitate separating the device 10 into parts. For example, the frame can be grooved along a line, as shown at 52.1 and 52.2 in FIG. 6 which is on line A—A. For taking an impression of posterior teeth only, the center anterior portion 36 of the film 12 can be removed.

Figure 4A:
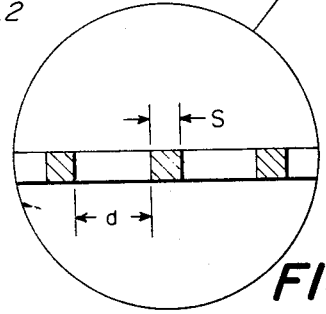
FIG. 4A is an enlarged detail of FIG. 4.

Pastes for taking bite registrations are available in forms which are soft when applied, and then harden in the mouth responsive to hygroscopic changes. The paste 54 shown in FIG. 4 may be such a paste, or any other suitable paste. Layers of the paste are applied to both sides 16, 18 of the film 12 and the paste extends through the perforations 14. The film material separating the perforations, as shown at 56, 56, is thin also in the plane of the film, so that the film is readily frangible when the occlusal surfaces of the maxillary and mandibular arches apply pressure to the paste 54. Thus, for example as seen in FIG. 4A, the holes 14, if round, may have a diameter "d" between about 1.5 mm. to 2.0 mm., while the thickness "s" of the film material between two adjacent holes may be 1 mm. or less. The film 12 itself may be about 0.020 mm. thick. The nerves that are sensitive to touch, called "proprio-ceptors", will alter the bite, however minutely, when they feel pressure. For that reason, a carrier for the paste which is made of gauze or other woven fiber material, or of a film which is strong enough to exert a back pressure such as Shpuntoff's is not suitable for taking impressions with the highest fidelity to the existing bite of a patient. In the present invention the film 12 is readily frangible where present between occluding teeth, so as to minimize creating a reaction which will bring these nerves into play. It is intended in this invention that the film 12 shall function, for all practical purposes, solely as a carrier for the paste, creating a minimum of reactive force on the paste 54 in response to interdental pressure. The present invention thus provides a greater sensitivity to the contours of the occlusal surfaces than has heretofore been available, and provides a tool enabling the skilled restorative dentist to make fine adjustments in a restoration.

FIG. 5 shows an arrangement useful for making wax impressions of a bite. In this use of the invention the wax 64 is preferably a wax that is slow to set up, in order to provide adequate time to prepare the bite registration device and to take the impression. Ordinary dental waxes are made sticky by heating them, and become very hard and brittle when cooled. To facilitate use of a soft wax, the film 12 is preferably coated on each side 16, 18 with a layer 66, 68, respectively, of an adhesive material, having suitable nontoxic properties. These layers are very thin. The adhesive serves to aid the perforations 14 in holding the wax to the foil, and thereby make it possible to use a wax that is not itself sticky. Such a wax can respond to fine details in the occlusal surfaces of confronting teeth without sticking to the teeth. In combination with the readily frangible foil 12, the wax can provide superior sensitivity to such fine details.

Figure 7:
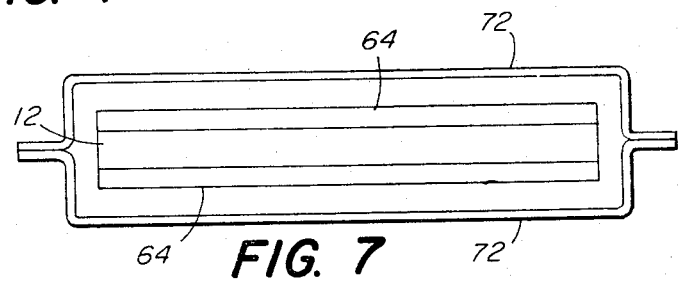
FIG. 7 schematically illustrates a prefabricated package including a bite registration device according to the invention.

A suitable wax for this purpose is that known as "Iowa" wax, a paraffin wax which is translucent when hard and opaque when soft, and which softens when heated. This wax is an accepted dental material, as recognized by the American Dental Association. A prefabricated structure according to FIG. 5, without the frame 22, is illustrated schematically in FIG. 7, with a protective enclosure 72 which is intended to be removed before the device is used. This device can be kept at room temperature or in a refrigerator prior to use, and to use it, after removing the enclosure 72 it may be dipped in water at about 140° F. to soften the wax 64 without causing it to flow; this condition will become apparent when the wax becomes opaque. The device is then placed to take the desired impression, the opposing arches or sections are closed on it, and then cold water may be applied to set the wax hard; that condition will become apparent when the wax becomes translucent.

The frangible foil 12 can be made of a paper material, a plastics material or a metal foil. The strength of the foil material itself is removed as a consideration by making the foil into a web by perforating it, for example as described above, so that the foil material between perforations is readily frangible. The impression material extends through the perforations so that in large measure the device is substantially entirely impression material adapted to be held in place by a carrier which has little or no significant ability to bring the proprioceptors into play when it is used in the mouth of a patient. While the frame 22 is useful for handling and manipulating the device, the invention contemplates that devices employing it may be supplied in the form of sheets or pieces without frames, in particular if the impression material is of a type that is adequately firm when cold so that it can be packaged, shipped and handled before it is used, like Iowa wax. Thus both devices which are coated with impression material by the dentist just prior to use, and prefabricated devices combining impression material and a frangible carrier, are within the scope of this invention.

With the present invention, it is possible to do check bites in plaster, for equalibrating full dentures (upper and lower) in the laboratory. A frangible carrier 12 will then be coated on each side with a thin layer of a plaster which hardens, and an accurate cast of the bite can be made. The particular form of perforations used is widely variable; holes or slits can be used, holes being preferred to minimize the quantity of carrier film that will be present.

In the carrier 12, the perforations 14 may take any desired shape—e.g.: round, square, rectangular, triangular or parallelogram. In any event, the septal thickness in distance "s" (see FIG. 5) should be small enough to assure that in use the carrier will minimally stimulate the proprioceptors associated with the teeth of which an occlusal impression is to be taken; preferably there will be no noticeable stimulation of these nerves, and the fidelity or accuracy of the impression will be more reliable than has up to now been possible. Use of a carrier 12 having elongated perforations 14 will facilitate deflection of the septal film material 56 between perforations in the plane of the carrier, between two closing occlusal surfaces, and to the extent that the septal regions can be deflected in this manner they will not stimulate the proprioceptors associated with those closing surfaces.

I claim:

1. A bite registration device for introducing bite registration material between the occlusal surfaces of teeth comprising a non-woven sheet of foraminous film having on each of its surfaces an adhesive material for holding a wax, said film being perforated over the major portion of its surfaces providing a septal distance between perforations so small that the material of said film between perforations is readily frangible under occlusal pressure on a registration material carried by said film so that it substantially lacks the ability to stimulate the proprioceptors associated with the teeth of which an occlusal impression is to be taken.

2. A device according to claim 1 having a wax on each of said surfaces.

3. A device according to claim 2 including a protective cover for storing the device until used.

4. A device according to claim 1 wherein said film is perforated over more than one-half of its surface.

5. The device according to claim 1 in combination with a bite registration material on both surfaces of said film and joined through the perforations in said film.

6. A device according to claim 1 including frame means peripherally supporting said film.

7. A device according to claim 6 for full-dental-arch use wherein said frame means is shaped to the outer periphery of a full arch and to the inner periphery of the posterior lateral teeth in both quadrants, and said film is generally U-shaped spanning the frame means at said quadrants and extending from said frame means at the anterior part of said outer periphery toward said frame means at said inner periphery in the region of the anterior teeth.

8. A device according to claim 1 wherein said carrier is made of a material selected from plastics, paper and metal films.

* * * * *